US00PP10609P

United States Patent [19]

Zaiger et al.

[11] Patent Number: Plant 10,609

[45] Date of Patent: Sep. 22, 1998

[54] PEACH TREE 'TUOLUMNE'

[76] Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, Calif. 95358

[21] Appl. No.: 878,548

[22] Filed: Jun. 5, 1997

[51] Int. Cl.[6] ..... A01H 5/00

[52] U.S. Cl. ..... Plt./43.1

[58] Field of Search ..... Plt./43.1

*Primary Examiner*—James R. Feyrer

[57] ABSTRACT

A new and distinct variety of peach tree (*Prunus persica*) with the following unique combination of features that are desirable in a new variety:

1. Vigorous, upright growth.
2. Regular and heavy production of fruit.
3. Relatively uniform size of fruit throughout tree.
4. Relatively even ripening of fruit throughout tree.
5. Firm, non-melting flesh that is suitable for mechanical pitters for stone removal.
6. Fruit that maintains good texture, shape and appearance after being canned.
7. Fruit with good flavor and eating quality, both fresh and after canning.

1 Drawing Sheet

ORIGIN OF THE VARIETY

The present new variety of peach tree was originated by us in our experimental orchard located near Modesto, Calif., as a first generation cross between two selected seedlings with field identification numbers 57GA963 and 14HA602. The maternal parent (57GA963) originated from a cross of a non-melting peach of unknown parentage with Andross Peach (non-patented). The paternal parent (14HA602) originated as a selected seedling from an open pollinated Diamente Peach (non-patented) seed. A large group of these first generation seedlings were planted and grown under careful observation by us, during which time one such seedling which represents the present variety, being especially desirable in its tree and fruit characteristics described above, was selected for reproduction and commercialization.

ASEXUAL REPRODUCTION OF THE VARIETY

Asexual reproduction of the new and distinct variety of peach tree was by budding, as performed by us in our experimental orchard located near Modesto, Calif., and shows that all characteristics of the tree and its fruit run true to the original tree and are established and transmitted through succeeding asexual propagations.

SUMMARY OF THE VARIETY

The new and distinct variety of peach tree is of large size, vigorous, upright growth, being a regular and productive bearer of medium size, non-melting, yellow flesh clingstone fruit. The fruit is further characterized by having firm flesh, relatively uniform ripening throughout the tree, having good handling and shipping quality, and maintaining excellent shape, texture and appearance after being canned. In comparison to Andross Peach (non-patented) this variety has more vigor, heavier production of firmer, non-melting yellow flesh fruit which are more resistant to bruising and browning, and is 4 to 6 days later in maturity.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of peach tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Form.*—Upright, normally pruned to vase shape.
- *Productivity.*—Productive.
- *Bearer.*—Regular.
- *Density.*—Medium dense.

Trunk:
- *Size.*—Medium to stocky.
- *Texture.*—Medium shaggy.
- *Color.*—Brown to tobacco brown (5-E-5) to (5-F-6).

Branches:
- *Size.*—Medium.
- *Texture.*—Smooth to medium rough, varies with age of growth.
- *Lenticels.*—Medium number. Medium size.
- *Color.*—Light brown to brown.

Leaves:
- *Size.*—Large. Average length 6". Average width 1⅜".
- *Form.*—Lanceolate. Acutely pointed.
- *Margin.*—Crenate.
- *Thickness.*—Medium.
- *Surface.*—Smooth.
- *Petiole.*—Medium length. Medium thickness.
- *Glands.*—Globose. Large size. Number varies from 2 to 6. Average number 4. Position on upper portion of petiole and the base of the leaf blade.
- *Color.*—Upper surface — green to deep green (28-E-5) to (28-F-7). Lower surface — dull green to green (28-E-4) to (28-E-6).

Flower buds:
- *Size.*—Medium.

*Form.*—Plump.
*Pubescence.*—Pubescent.

Flowers:
*Size.*—Medium, non-showy.
*Pollen.*—Present, self-fertile.
*Blooming period.—Date of first bloom.*—Feb. 20, 1996.
*Date of last bloom.*—Feb. 27, 1996. Varies slightly with climatic conditions.
*Color.*—Pink.

Fruit:
*Maturity when described.*—Firm ripe.
*Date of first picking.*—Jul. 29, 1996.
*Date of last picking.*—Aug. 2, 1996. Varies slightly with climatic conditions.
*Size.*—Medium. Average diameter axially 2¼" to Average transversely in suture plane 2½" to 2⅝".
*Form.*—Nearly globose, slightly flattened at stem end.
*Suture.*—Shallow, extends from base to apex.
*Ventral surface.*—Slightly lipped at suture line. Varies from slightly lipped to rounded.
*Apex.*—Usually round, some fruit with very slight apical point.
*Base.*—Retuse.
*Cavity.*—Slightly elongated in suture plane. Average depth ½". Average breadth ¾".

Flesh:
*Ripens.*—Evenly.
*Texture.*—Very firm, non-melting, shows a high degree of resistance to browning.
*Fibers.*—Few, small and tender.
*Aroma.*—Slight.
*Juice.*—Light to moderate.
*Eating quality.*—Good.
*Flavor.*—Good, both fresh and canned.
*Color.*—Yellow to yellowish orange (4-A-6) to (4-A-8).

Skin:
*Thickness.*—Medium.
*Texture.*—Medium.
*Down.*—Moderate.
*Tendency to crack.*—None.
*Color.*—Yellow ground color (4-A-6) to (4-A-8), very slight red blush (10-C-6) to (10-C-8).

Stone:
*Type.*—Clingstone.
*Size.*—Large. Length 1¼". Width 1". Thickness ¾.
*Form.*—Primarily ovoid, varies from ovoid to obovoid.
*Base.*—Varies from straight to rounded.
*Apex.*—Usually rounded, varies from rounded to slight point.
*Surface.*—Irregularly furrowed toward apex, pitted toward base. Both the furrows and pits are shallow in depth.
*Sides.*—Equal to unequal.
*Tendency to split.*—None.
*Color.*—Dark brown to reddish brown (8-F-6) to (8-F-7).

Use: Canned.
Keeping quality: Good, both as fresh and after processing.
Shipping quality: Good.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of peach tree, substantially as illustrated and described, characterized by its large size, vigorous, upright growth and a regular and productive bearer of medium size, non-melting, yellow flesh, clingstone fruit, which after being canned, has the ability to maintain good shape, texture, and eating quality; this variety is further characterized by being relatively uniform in maturity and size throughout the tree and, in comparison to Andross Peach (non-patented), is more vigorous, has greater production of firmer, non-melting yellow flesh fruit, and is approximately 4 to 6 days later in maturity.

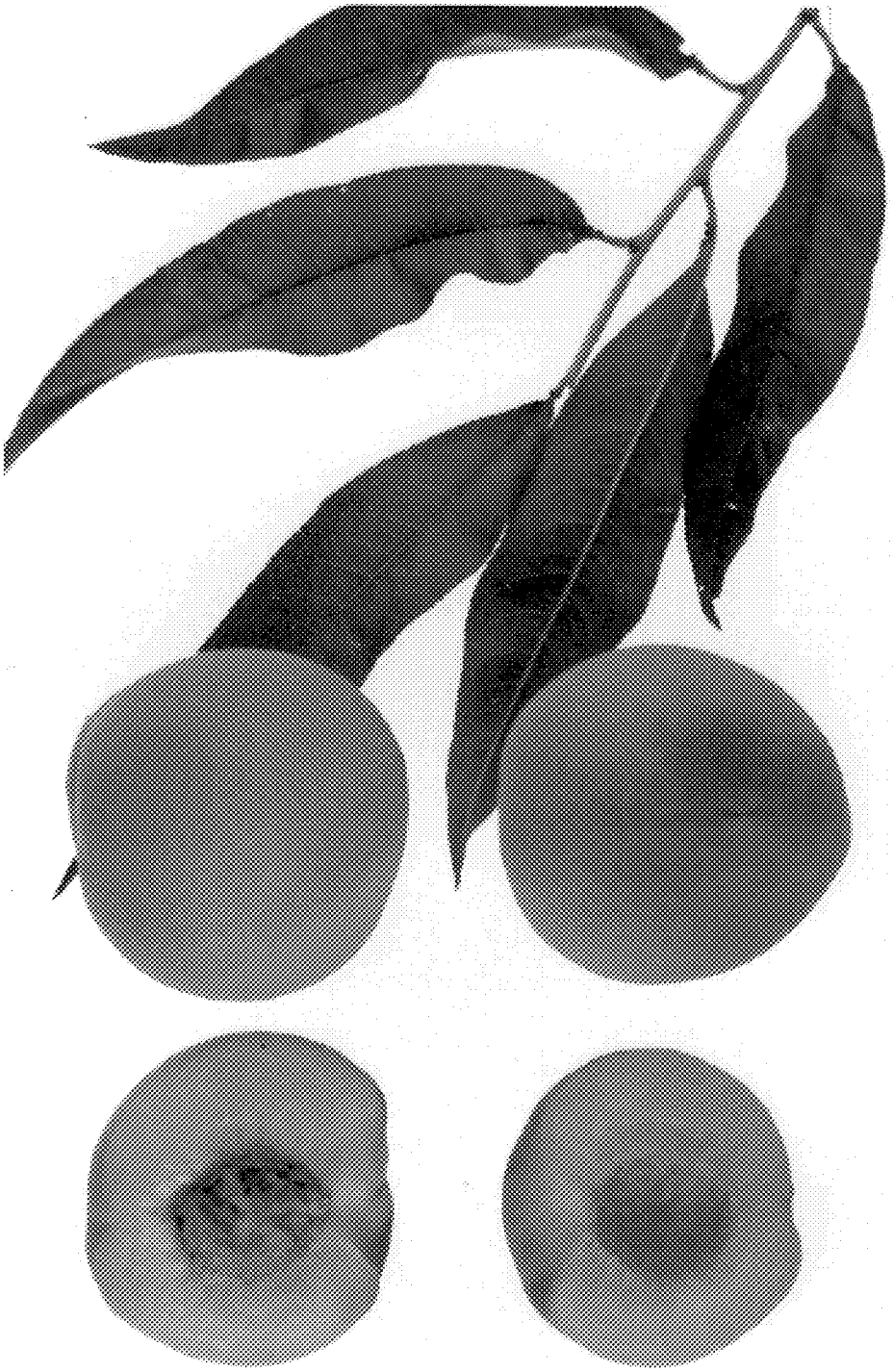

* * * * *